United States Patent
Rodriguez-Ponce (10) Patent No.: US 10,052,161 B2
(45) Date of Patent: Aug. 21, 2018

(54) BRAIN SHIFT COMPENSATION FOR CATHETER TRAJECTORY PLANNING

(71) Applicant: Brainlab AG, Munich (DE)

(72) Inventor: Maria Inmaculada Rodriguez-Ponce, Feldkirchen (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 15/500,642

(22) PCT Filed: Aug. 6, 2014

(86) PCT No.: PCT/EP2014/066916
§ 371 (c)(1),
(2) Date: Jan. 31, 2017

(87) PCT Pub. No.: WO2016/019991
PCT Pub. Date: Feb. 11, 2016

(65) Prior Publication Data
US 2017/0215968 A1 Aug. 3, 2017

(51) Int. Cl.
*A61B 34/10* (2016.01)
*A61B 5/00* (2006.01)
*A61B 6/00* (2006.01)

(52) U.S. Cl.
CPC ............ *A61B 34/10* (2016.02); *A61B 5/0042* (2013.01); *A61B 6/52* (2013.01); *A61B 2576/026* (2013.01); *G06T 2207/20004* (2013.01); *G06T 2207/30016* (2013.01); *G06T 2207/30021* (2013.01)

(58) Field of Classification Search
None
See application file for complete search history.

(56) References Cited

U.S. PATENT DOCUMENTS

| | | | |
|---|---|---|---|
| 2009/0118638 A1 | 5/2009 | Luis et al. | |
| 2013/0085344 A1* | 4/2013 | Merkl | G06F 19/3437 600/300 |
| 2013/0279784 A1 | 10/2013 | Streatfield et al. | |

FOREIGN PATENT DOCUMENTS

EP          1980201 A2     10/2008

OTHER PUBLICATIONS

Skrinjar,O et al., "Model-driven brain shift compensation", Article, Medical Image Analysis, pp. 361-373, Jan. 2002, USA.
(Continued)

*Primary Examiner* — Justin P. Misleh
(74) *Attorney, Agent, or Firm* — Tucker Ellis LLP (57) ABSTRACT

The present invention relates to compensating for brain shift in catheter trajectory planning. First brain shift information is determined from an initial brain image dataset, an initial planning dataset, a patient orientation dataset, and first burr hole dataset. The brain image dataset is updated based on the first brain shift information and a trajectory of a first catheter is updated based on the updated brain image dataset. For a subsequent catheter placement, subsequent brain shift information is determined based on the updated brain image dataset, the patient orientation dataset, and a subsequent burr hole dataset. The brain image dataset is updated again based on the subsequent brain shift information. The re-updated brain image dataset is utilized to update trajectories of the subsequent catheter as well as any preceding catheters.

14 Claims, 3 Drawing Sheets

(56) References Cited

OTHER PUBLICATIONS

Soza, G., "Registration and Simulation for the Analysis of Intraoperative Brain Shift" Dissertation, 2005, pp. 1-212, The Friedrich-Alexander-Universtat Erlangen-Nurnberg, Germany.

Winkler, D. et al., "The first evaluation of brain shift during functional neurosurgery by deformation field analysis" Article, Journal of Neurology, Neurosurgery & Psychiatry, 2005, pp. 1161-1163, Germany.

Wittek, A. et al., "Brain Shift Computation Using a Fully Nonlinear Biomechanical Model", Medical Image Computing and Computer-Assisted Intervention—MICCAI 2005, Lecture Notes in Computer Science vol. 3750, 2005, pp. 583-590, Springer-Verlag Berlin Heidelberg.

Hu, J. et al., "Intraoperative brain shift prediction using a 3D inhomogeneous patient-specific finite element model", Article, Journal of Neurosurgery, Jan. 2007 vol. 106, pp. 164-169, Detroit, Michigan.

Miller, K., et al.,"Biomechanics of the brain for computer-integrated surgery", Original Paper, Acta of Bioengineering and Biomechanics, vol. 12, No. 2, 2010, pp. 25-37, Warsaw.

International Search Report and Written Opinion, dated May 19, 2015, pp. 9, European Patent Office, NL.

\* cited by examiner

BRAIN SHIFT COMPENSATION FOR CATHETER TRAJECTORY PLANNING

RELATED APPLICATION DATA

This application is a national phase application of International Application No. PCT/EP2014/066916, filed Aug. 6, 2014 and published in the English language.

The present invention relates to a method, a computer program and a system for planning trajectories of at least two catheters by taking into account a brain shift which is caused by the catheters and/or the openings for the catheters.

Many medical treatments, such as infusions in a cancer treatment, require the placement of one or more catheters. Prior to actually placing the catheters, planning of the trajectories of the catheters is performed. Each catheter is assigned a target point at which the distal end of the catheter shall be located after its placement. Depending on the application, all target points can be the same, all target points can be different or two or more catheters can have the same target point. A treatment plan then in many cases defines how an infusate is infused by use of the catheters.

If the target points are located in the brain of a patient, then it is typically necessary to create openings in the cranium in order to place the catheters therethrough. Those openings are also referred to as burr holes.

The present invention takes into account that the brain deforms during placement of the catheters and adapts the planning of the trajectories accordingly. The deformation of the brain is also referred to as brain shift. Brain shift can have several causes, such as a mechanical deformation caused by insertion of a catheter. Another cause is that a burr hole is a vent such that a vacuum which would hold the brain in place inside the cranium cannot build up. The burr hole therefore causes a brain shift within the cranium.

The present invention relates to a method for planning trajectories of at least two catheters, wherein each trajectory ends at a target point which is associated with a corresponding catheter which is one of said catheters and is located within a brain which is in turn located in a cranium. As indicated above, the target points associated with the catheters can be a single target point, different target points for each of the catheters or two or more catheters can have the same target point.

A first step a) of the method involves acquiring an initial brain image dataset which represents a three-dimensional image of at least a part of the brain. The initial brain image dataset is obtained using a suitable imaging modality, such as a magnetic resonance imaging modality.

A second step b) involves acquiring an initial planning dataset which represents initial trajectories of the catheters. The initial planning dataset in particular was determined on the basis of the initial brain image dataset, and in particular represents initial trajectories of the catheters, wherein the initial trajectories have preferably been determined without considering any brain shift. The initial trajectories preferably end at the target points which are associated with the catheters. Those target points are for example distributed around a tumor within the brain.

A third step c) involves acquiring a patient orientation dataset which represents the orientation of the cranium. The orientation of the cranium in particular means the orientation of the cranium with respect to a gravity vector which points into the direction of the force of gravity. In other words, the patient orientation dataset contains the information in which direction the force of gravity acts onto the brain.

A fourth step d) involves acquiring a first burr hole dataset which represents the size and location of a first burr hole in the cranium for a first catheter. The first burr hole dataset preferably is a part of or is derived from the initial planning dataset. For example, the center of the burr hole is the point at which the trajectory of the corresponding catheter passes through the cranium. The size of the first burr hole can be a predefined size or a size depending on the properties of the corresponding catheter.

A fifth step e) involves calculating a first brain shift dataset from the initial brain image dataset, the patient orientation dataset and the first burr hole dataset, wherein the first brain shift dataset at least represents a brain shift which would be caused by the first burr hole. As explained above, the first burr hole connects the inside and the outside of the cranium, thus enabling air flow and thus a pressure compensation. In general, the force of gravity acts upon the brain. Without a burr hole, the movement (or deformation) of the brain within a cranium due to the force of gravity is limited because a movement (or deformation) of the brain would cause a vacuum, which counteracts the movement (or deformation) of the brain. This counteraction does not occur if the burr hole enables the pressure compensation, such that the brain moves (or deforms) in the direction of the force of gravity once the burr hole is created.

The brain shift caused by a burr hole is preferably calculated using a finite element method which models the brain tissue and the influence of gravity on the brain tissue and counter-forces caused by vacuum as well as the loss of counter-forces due to the burr hole. Many approaches for calculating a brain shift are known to the skilled person. Different examples can be found in the following documents, all of which are incorporated by reference: Skrinjar, O., Nabavi, A., Duncan, J.: *Model-driven brain shift compensation*, Medical Image Analysis 6(4), 361-373 (2002); Soza, G.: *Registration and Simulation for the Analysis of Intraoperative Brain Shift*, 2005, dissertation at the Friedrich-Alexander-Universität Erlangen-Nürnberg; Winkler, D., Tittgemeyer, M., Schwarz, J. et al., *The first evaluation of brain shift during functional neurosurgery by deformation field analysis*, Journal of Neurology, Neurosurgery & Psychiatry, 2005;76:1161-1163; Wittek, A., Kikinis, R., Warfield, S., Miller, K., *Brain Shift Computation Using a Fully Nonlinear Biomechanical Model*, Medical Image Computing and Computer-Assisted Intervention—MICCAI 2005, Lecture Notes in Computer Science Volume 3750, 2005, pp 583-590; Hu, J., Jin, X., Lee, J. et al., *Intraoperative brain shift prediction using a 3D inhomogeneous patient-specific finite element model*, Journal of Neurosurgery, 2007 Jan;106(1):164-9; Miller, K., Wittek, A., Joldes G., *Biomechanics of the brain for computer-integrated surgery*, Acta of Bioengineering and Biomechanics. Original paper. Vol. 12, No. 2,2010.

A sixth step f) involves calculating an updated brain image dataset from the initial brain image dataset and the first brain shift dataset. The updated brain image dataset represents a three-dimensional image of at least a part of the brain if the calculated brain shift represented by the first brain shift dataset occurs. One implementation for calculating the updated brain image dataset is to shift the voxels of the initial brain image dataset in accordance with the first brain shift dataset. The brain shift also causes a shift of the target points relative to the cranium, and the updated brain image dataset comprises the updated locations of the target points.

A seventh step g) involves updating the trajectory of the first catheter on the basis of the updated brain image dataset.

In particular, the trajectory corresponding to the first catheter in the initial planning dataset is amended such that the trajectory ends at the corresponding target point in the updated brain image dataset.

After the seventh step g) of the method, an updated planning dataset exists in which the trajectory of the first catheter is adapted to the influence of the first burr hole on the brain, and therefore on the position of the target point within the cranium.

An eighth step h) involves acquiring a subsequent burr hole dataset which represents the size and location of a subsequent burr hole in the cranium for a subsequent catheter. The meaning of the subsequent burr hole dataset is the same as the meaning of the first burr hole dataset, but regarding a different burr hole.

A ninth step i) involves calculating a subsequent brain shift dataset from the updated brain image dataset, the patient orientation dataset and the subsequent burr hole dataset, wherein the subsequent brain shift dataset at least represents a brain shift which would be caused by the subsequent burr hole. The calculation is basically the same as in step e), but is based on the updated brain image dataset instead of the initial brain image dataset and the subsequent burr hole dataset instead of the first burr hole dataset.

A tenth step j) involves updating the updated brain image dataset on the basis of the subsequent brain shift dataset. This step is basically the same as step g) and results in a second generation updated brain image dataset, which is also referred to as re-updated brain image dataset.

An eleventh step k) involves updating the trajectory of the subsequent catheter and all preceding catheters on the basis of the re-updated brain image dataset, wherein a preceding catheter is a catheter whose trajectory has been updated in a preceding step of the method. So if there is only one subsequent burr hole, that is a second burr hole for a second catheter, then the trajectory of the first and the second catheter are updated.

The updating step k) is different from the updating step g) in that not only the trajectory of a single catheter is updated, but the trajectory of the subsequent catheter as well all trajectories which have previously been updated for other catheters. In other words, the updating step k) relates to all catheters which have been considered so far.

In one embodiment of the invention, steps h) to k) are repeated for at least one other subsequent catheter. This means that steps h) to k) are iterated for all catheters for which the trajectories are to be planned. So if for example a third catheter, which is the second subsequent catheter, is considered, the updating step k) in the second iteration, that is the iteration corresponding to the third catheter, updates both the trajectory of the subsequent catheter (the third catheter) as well as the preceding catheters (catheters 1 and 2).

In one embodiment, the subsequent brain shift dataset calculated in step i) also represents a brain shift caused by at least one preceding catheter. As explained above, the actual placement of a catheter would cause a brain shift along the trajectory, for example by pushing the brain tissue with the tip of the catheter or by a friction of the brain tissue along the catheter. In this embodiment, this aspect of the brain shift is accounted for. Preferably, the subsequent brain shift dataset represents a brain shift caused by all of the preceding catheters.

In one embodiment, the subsequent brain shift dataset calculated in step i) also represents a brain shift caused by an infusion performed using at least one preceding catheter. An infusion causes a brain shift since the infusate displaces the brain tissue. Typically, a backflow along the catheter causes a cylindrical radial displacement of the brain tissue, while an accumulation of the infusate at the distal end of the catheter causes a spherical radial displacement of the brain tissue. Preferably, the subsequent brain shift dataset represents the brain shift caused by infusions performed using all preceding catheters.

In one embodiment, calculating the subsequent brain shift dataset in step i) involves considering the structural properties of at least one preceding catheter. The structural properties in this document in particular comprise the diameter and/or the rigidity of a catheter. If a catheter is placed, it influences the brain shift which is caused by a subsequently made burr hole and/or a subsequently placed catheter. In particular, a preceding catheter reinforces the brain tissue and therefore reduces the brain shift of a subsequent burr hole and/or catheter, at least around it.

In one embodiment, updating the trajectory in step k) involves considering the structural properties of at least one preceding catheter. The catheter for which the trajectory is updated in step k) is referred to as the current catheter. This embodiment is of particular advantage if the distal end of said preceding catheter moves due to the brain shift caused by the burr hole corresponding to the current catheter. The effect of this movement might be compensated for by adapting the target point of the current catheter accordingly and further by optionally adapting the treatment plan. The adapted target point of the current catheter results in a trajectory which is different from the trajectory as obtained without considering the structural properties of at least one preceding catheter.

In one embodiment, steps h) to k) are repeated for the same subsequent catheter, but with an amended subsequent burr hole dataset. This means that a particular iteration is repeated for the same catheter, but a different corresponding burr hole is assumed. This embodiment is of particular relevance because the burr hole, in particular the position and/or the size of the burr hole, can be varied in order to optimize the planning, in particular if the calculated brain shift is such that the initial planning for the burr hole is no longer viable.

In one embodiment, the method further comprises the steps of acquiring a treatment plan and of updating the treatment plan on the basis of the updated trajectories. A treatment plan in particular comprises the amount of infused infusate over time in order to achieve a desired effect, in particular on a tumor. The acquired treatment plan was in particular generated on the basis of the initial planning dataset in order to optimize the infusion. Due to the updated trajectories which are represented by the updated planning dataset, the acquired treatment plan might become obsolete. In this embodiment, an updated treatment plan is determined which accounts for the updated trajectories and optionally the updated brain image dataset.

In one embodiment, the method further comprises the step of checking at least one updated trajectory for compliance with planning guidelines which represent constraints for the trajectory. A typical constraint for a trajectory is the distance to a structure at risk, such as a vessel or functional area of the brain. The initial planning dataset typically complies with all planning guidelines. However, an updated trajectory, and optionally in combination with the updated brain image dataset, might no longer comply with a planning guideline. If non-compliance of an updated trajectory with a planning guideline is determined, the method might at least one of trigger an alarm or repeat the planning with an amended burr hole dataset corresponding to the catheter whose trajectory no longer complies with a planning guideline. The method can therefore preferably be repeated until all updated trajectories comply with all planning guidelines.

In the explanations made so far, it was assumed that there is a dedicated burr hole for each catheter. However, in one embodiment, more than one catheter is to be inserted through the same burr hole. In this embodiment, updating the trajectory of the first catheter in step g) or the trajectory of the subsequent catheter in step k) involves updating the trajectories of two or more catheters which are to be inserted through the same burr hole. This means that the trajectories of a plurality or all of the catheters which are to be inserted through the same burr hole are updated before the trajectories of the catheter or catheters to be inserted through a subsequent burr hole or subsequent burr holes are updated. In other words, this embodiment updates the trajectories burr hole by burr hole.

Preferably, updating the trajectories of two or more catheters which are to be inserted through the same burr hole is performed sequentially for the two or more catheters, and updating the trajectory of a second or a subsequent catheter which is one of said two or more catheters involves calculating a brain shift dataset representing a brain shift caused by at least one preceding catheter which is one of said two or more catheters and updating the updated brain image dataset according to the calculated brain shift dataset. In other words, the trajectories of two or more catheters which are to be inserted through the same burr hole is not performed on the basis of the same updated brain image dataset. A brain shift dataset is calculated instead once the trajectory of one of the catheters is updated. The updated brain image dataset is then updated, and the updated brain image dataset is then used for updating the trajectory of the next catheter of the same burr hole. This accounts for the fact that trajectories of catheters which are to be inserted through the same burr hole are typically very close to each other. The brain shift which is caused by a catheter which has already been placed therefore has an increased influence of a subsequent catheter which is to be placed through the same burr hole. This embodiment therefore considers the brain shift caused by such a catheter when updating the trajectory of a subsequent catheter.

The present invention further relates to a computer program which, when running on a computer, causes the computer to perform the method as explained above and/or to a program storage medium on which the program is stored, for example in a non-transitory form.

The present invention further relates to a system for planning trajectories of at least two catheters, wherein each trajectory ends at a target point which is associated with a corresponding catheter which is one of said catheters and is located within a brain which is in turn located in a cranium. The system comprises a computer on which the program as explained above is stored and/or run.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which in particular comprises technical, in particular tangible components, in particular mechanical and/or electronic components. Any device mentioned as such in this document is a physical and in particular tangible device.

In the field of medicine, imaging methods (also called imaging modalities and/or medical imaging modalities) are used to generate image data (for example, two-dimentional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, in particular volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices in particular are used to generate the image data in apparatus-based imaging methods. The imaging methods are for example used for medical diagnostics, to analyse the anatomical body in order to generate images which are described by the image data. The imaging methods are also in particular used to detect pathological changes in the human body. However, some of the changes in the anatomical structure, in particular the pathological changes in the structures (tissue), may riot be detectable and in particular may not be visible in the images generated by the imaging methods. A tumour represents an example of a change in an anatomical structure. If the tumour grows, it may then be said to represent an expanded anatomical structure. This expanded anatomical structure may not be detectable; in particular, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and in particular discernible in the image generated by the imaging method. In addition to these tumours, referred to as "enhancing"tumours, it is thought that approximately 10% of brain tumours are not discernible on a scan and are in particular not visible to a user looking at the images generated by the imaging method.

The method in accordance with the invention is in particular a data processing method. The data processing method is preferably performed using technical means, for example a computer. The data processing method is preferably constituted to be executed by or on a computer and in particular is executed by or on the computer. In particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or which are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer.

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The method in accordance with the invention is preferably at least partly executed by a computer, i.e. all the steps or merely some of the steps (i.e. less than the total number of steps) of the method in accordance with the invention can be executed by a computer.

In particular, the invention does not involve or in particular comprise or encompass an invasive step which would represent a substantial physical interference with the body requiring professional medical expertise to be carried out and entailing a substantial health risk even when carried out with the required professional care and expertise. In particular, the invention does not comprise a step of positioning or placing a catheter. More particularly, the invention does not involve or in particular comprise or encompass any surgical or therapeutic activity. The invention is instead directed in particular to planning trajectories of catheters, preferably before the placement of the catheters begins or going along with placing the catheters so as to adapt the planning on the fly. For this reason alone, no surgical or therapeutic activity and in particular no surgical or therapeutic step is necessitated or implied by carrying out the invention.

Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

It is within the scope of the present invention to combine one or more features of one or more embodiments in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can in particular be added to said other embodiment.

The present invention has particular application within the iPlan® radiotherapy planning software by Brainlab AG. By applying the present invention, the iPlan® software can account for brain shift caused by multiple burr holes, thus increasing the planning accuracy. In the following, the invention is described with reference to the enclosed figures which represent preferred embodiments of the invention. The scope of the invention is not however limited to the specific features disclosed in the figures.

Figure 1A:
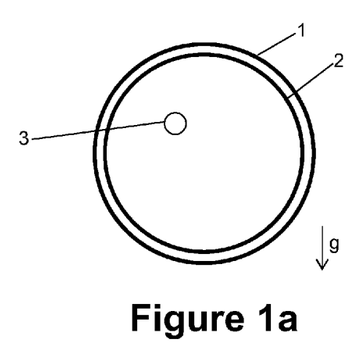
FIG. 1a an initial brain image dataset of a cranium, a brain and a tumor.

FIG. 1a schematically shows an initial brain image dataset which represents a three-dimensional image of a cranium 1 in which a brain 2 is located. Within the brain 2, there is a tumor 3 to be treated. The cranium 1, the brain 2 and the tumor 3 are depicted schematically be simplified outlines, and those items may not be drawn to scale.

The treatment of the tumor 3 involves placing at least two catheters with their distal ends in the vicinity of the tumor 3. Via the catheters, an infusate for treating the tumor 3 is to be infused. Planning the treatment of the tumor 3 therefore involves two aspects. The first aspect is planning the trajectories of the catheters such that they end at target points in the vicinity of the tumor 3. The second aspect is establishing a treatment plan which represents the amount of infusate to be infused by use of the respective catheters over time. The present invention mainly relates to planning of the catheter trajectories.

Figure 1B:
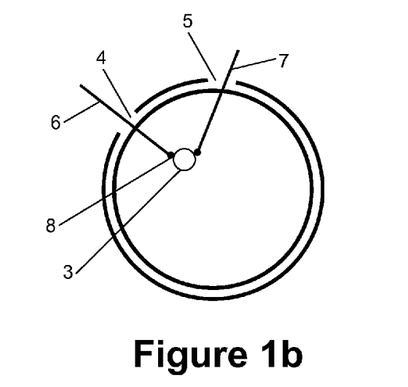
FIG. 1b the initial brain image dataset of FIG. 1a with an initial planning dataset.

Step a) of the method involves acquiring the initial brain image dataset as shown in FIG. 1a. Step b) involves acquiring an initial planning dataset which represents initial trajectories of the catheters. An exemplary initial planning dataset based on the initial brain image dataset is shown in FIG. 1b. The initial planning dataset comprises initial trajectories of catheters 6 and 7, wherein the trajectories end at target points 8 and 9, respectively. The initial planning dataset was obtained using classical approaches which do not consider a brain shift which is caused by the burr holes 4 and 5 needed for inserting the catheters 6 and 7 or caused by the placement of the catheters 6 and 7.

Method step c) involves acquiring a patient orientation dataset which represents the orientation of the cranium 1 with respect to the force of gravity, which is indicated in FIG. 1a as the vector g. Step d) involves acquiring a first burr hole dataset which represents the size and location of a first burr hole 4 in the cranium 1 for the first catheter 6.

Figure 1C:
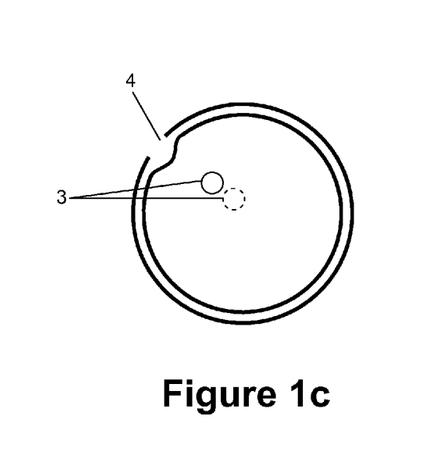
FIG. 1c a first updated brain image dataset.

Method step e) involves calculating a first brain shift dataset from the initial brain image dataset, the patient orientation dataset, in particular the direction of the force of gravity relative to a cranium 1, and the first burr hole dataset. The first brain shift dataset represents a brain shift which would be caused by the first burr hole 4 due to a loss of cerebrospinal fluid and gravity acting on the brain 2. The brain shift, which represents a movement and/or deformation of the brain 2, is indicated in FIG. 1c. It is represented by the amended shape of the brain 2. The brain shift also causes a movement of the tumor 3 relative to a cranium 1. The position of the tumor 3 without the brain shift is shown by solid circle, while the new position of the tumor 3 due to the first brain shift is indicated by a dashed circle. The target points 8 and 9 move together with the tumor 3. It shall be noted that shifts of the tumor 3 and the target points are exaggerated in order to accentuate them.

Method step f) involves calculating an updated brain image dataset from the initial brain image dataset and the first brain shift dataset. The updated brain image dataset is shown in FIG. 1c. It can be referred to as the first updated brain image dataset because it represents the brain shift caused by the first burr hole 4.

Due to the first brain shift, the trajectory of the first catheter 6 no longer ends at the desired target point. Method step g) therefore involves updating the trajectory of the first catheter 6 on the basis of the updated brain image dataset. In particular, a new trajectory is calculated which ends at the desired target point relative to the tumor 3.

Method step h) involves acquiring a subsequent burr hole dataset which represents the size and location of a second burr hole 5 in the cranium 1 for a second catheter. The second burr hole is a subsequent burr hole and the second catheter 7 is a subsequent catheter.

Method step i) involves calculating a second brain shift dataset from the updated brain image dataset shown in FIG.

Figure 1D:
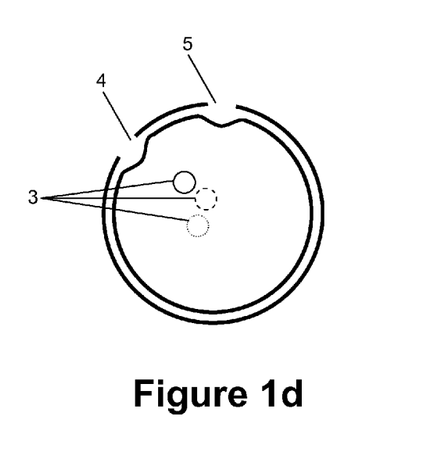
FIG. 1d a second updated brain image dataset.

1c, the patient orientation dataset and the second burr hole dataset. The second brain shift dataset represents a second brain shift which would be caused by the second burr hole 5. Step j) involves updating the updated brain image dataset on the basis of the second brain shift dataset. The updated version of the updated brain image dataset can be referred to as second updated brain image dataset. It is shown in FIG. 1d.

As can be seen from the second updated brain image dataset, the second brain shift caused by the second burr hole 5 results in another displacement of the tumor 3 relative to the cranium 1. The new position of the tumor 3 due to the brain shifts caused by the burr holes 4 and 5 is shown as a dotted circle in FIG. 1d. The displacement of the tumor 3 means that the updated trajectory of the first catheter 6 and the initial trajectory of the second catheter 7 no longer end at the desired target points relative to the tumor 3. Method step k) therefore involves updating the trajectories of the first catheter and the second catheter on the basis of the second updated brain image dataset, such that both trajectories end at desired target points relative to the tumor 3.

In the present embodiment, the second brain shift is not only caused by the second burr hole 5, but also by the placement of the first catheter 6, which also causes a deformation of the brain 2. In general, a brain shift is calculated from a tissue model, which is in particular a mesh. The brain is considered as an elastic body, such that a mathematical model of deformation can be applied. One exemplary model of deformation is described by the formula $$(\lambda+\mu)\nabla \text{div } u + \mu \Delta u = -f,$$

which is a Navier Lamé equation. With appropriate boundary conditions and parameters, such as forces due to gravity, gradient pressure due to loss of cerebrospinal fluid and catheter placement, the equation can be solved, for example using the finite element method.

Figure 2:
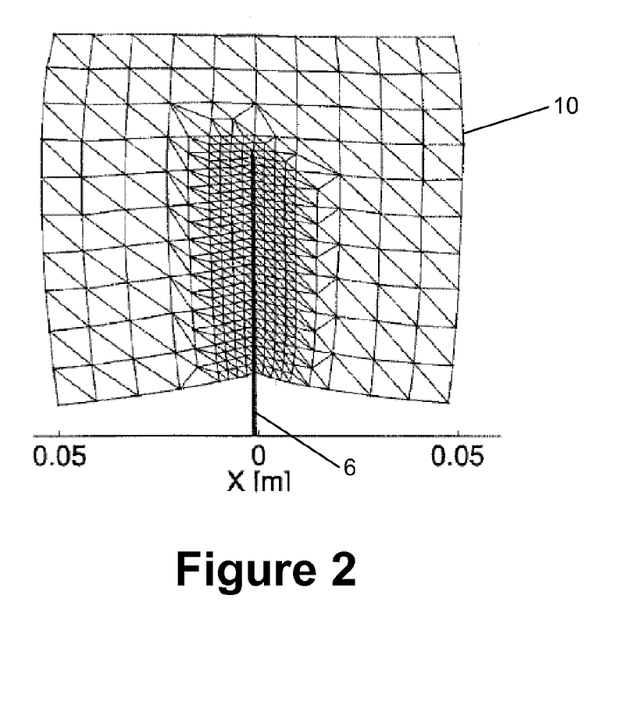
FIG. 2 a tissue model for calculating a brain shift

An example for a brain shift caused by catheter placement by use of a mesh model is shown in FIG. 2. This Figure shows a mesh 10 which represents a part of the brain tissue. When the catheter 6 is placed, the tissue is deformed by the tip of the catheter 6 pushing the tissue and the side of the catheter shifting the tissue due to frictional forces. The resulting brain shift is shown in FIG. 2.

Figure 3:
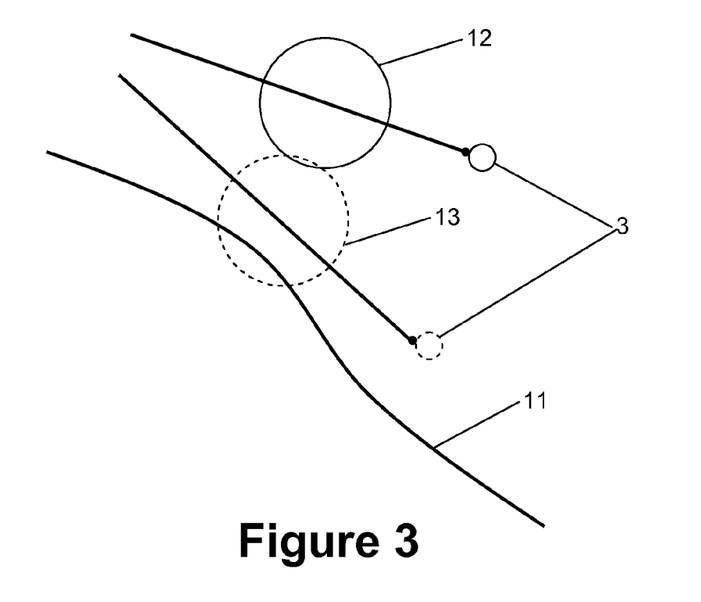
FIG. 3 a part of the initial brain image dataset with a structure at risk.

FIG. 3 shows the tumor 3 relative to a vessel 11 in its initial position as a solid circle and with an amended position due to the brain shifts as a dotted circle. The vessel 11 is a structure at risk, which means that the catheter 6 must not get closer to the vessel 11 than a predetermined minimum distance, which is a constraint for the trajectory. The minimum distance is shown as a circle 12, 13 around the catheter 6. As can be seen from FIG. 3, the initial trajectory complies with the planning guideline because it is far enough away from the vessel 11 as indicated by the solid circle 12. Due to the displacement of the tumor 3, the trajectory of the catheter 6 moves closer to the vessel 11. The minimum distance for the updater trajectory of the catheter 6 is indicated by a dotted circle. As can be seen from FIG. 3, the updated trajectory of the first catheter 6 is closer to the vessel 11 than the minimum distance indicated by the dotted circle 13. This means that the updated trajectory does no longer comply with the planning guidelines. The method for planning the trajectories of the catheter 6 and 7 is therefore repeated with a different initial planning dataset, and in particular with a different first burr hole dataset.

Figure 4:
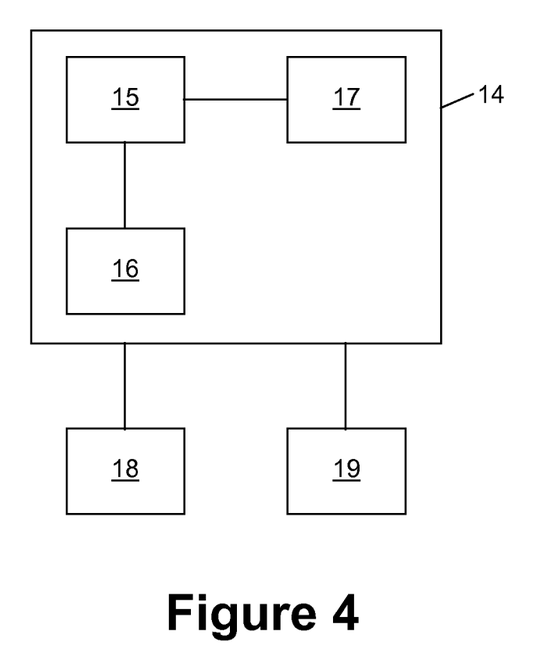
FIG. 4 a system for carrying out the invention.

FIG. 4 schematically shows a system for implementing the method described above. The system comprises a computer 14, an input unit 18, such as a keyboard, a mouse, a touchscreen or the like, and an output unit 19 such as a monitor. The computer 14 comprises a central processing unit 15, a memory unit and an interface 17. The memory unit 16 comprises a computer program which causes the central processing unit 15 to perform the method described herein. The central processing unit 15 acquires data, such as the initial brain image dataset, the initial planning dataset, the patient orientation dataset or a burr hole dataset, from the memory unit 16 or via the interface 17. The computer 14 is adapted to display data on the output unit 19, such as an updated brain image dataset or the initial or updated trajectories of the catheters.

The invention claimed is:

1. A system for planning trajectories for a plurality of catheters, wherein each planned trajectory runs through a portion of a cranium and a brain located in the cranium to a respective planned target point in the brain, the system comprising a computer having a processor configured to:
  a) acquire an initial brain image dataset, the initial brain image dataset representing a three-dimensional image of at least a part of the brain;
  b) acquire an initial planning dataset that includes a plurality of initial planned trajectories respectively corresponding to the plurality of catheters;
  c) acquire a patient orientation dataset that indicates an orientation of the cranium;
  d) acquire a first burr hole dataset for a first initial planned trajectory of the plurality of initial planned trajectories, the first burr hole dataset representing a size and a location of a first burr hole in the cranium corresponding to the first initial planned trajectory for a first catheter of the plurality of catheters;
  e) calculate a first brain shift dataset from the initial brain image dataset, the patient orientation dataset and the first burr hole dataset, wherein the first brain shift dataset represents a first estimated brain shift, the first estimated brain shift corresponding to a brain shift caused by opening the first burr hole in the cranium;
  f) calculate a first updated brain image dataset from the initial brain image dataset and the first brain shift dataset;
  g) update the first initial planned trajectory based on the first updated brain image dataset to generate a first updated planned trajectory;
  h) acquire a second burr hole dataset for a second initial planned trajectory of the plurality of initial planned trajectories, the second burr hole dataset representing a size and a location of a second burr hole in the cranium corresponding to the second initial planned trajectory for a second catheter of the plurality of catheters;
  i) calculate a second brain shift dataset from the first updated brain image dataset, the patient orientation dataset and the second burr hole dataset, wherein the second brain shift dataset represents a second estimated brain shift, the second estimated brain shift corresponding to a brain shift caused by opening the second burr hole in the cranium;
  j) update the first updated brain image dataset based on the second brain shift dataset to generate a second updated brain image dataset; and
  k) update the first updated planned trajectory and the second initial planned trajectory based on the second updated brain image dataset.

2. A method performed by a computer having a processor for planning trajectories for a plurality of catheters, wherein each planned trajectory runs through a portion of a cranium and a portion of a brain located in the cranium to a respective planned target point in the brain, the method comprising the steps of:
- a) acquiring, at the processor, an initial brain image dataset, the initial brain image dataset representing a three-dimensional image of at least a part of the brain;
- b) acquiring, at the processor, an initial planning dataset that includes a plurality of initial planned trajectories respectively corresponding to the plurality of catheters;
- c) acquiring, at the processor, a patient orientation dataset that indicates an orientation of the cranium;
- d) acquiring, at the processor, a first burr hole dataset for a first initial planned trajectory of the plurality of initial planned trajectories, the first burr hole dataset representing a size and a location of a first burr hole in the cranium corresponding to the first initial planned trajectory for a first catheter of the plurality of catheters;
- e) calculating, by the processor, a first brain shift dataset from the initial brain image dataset, the patient orientation dataset and the first burr hole dataset, wherein the first brain shift dataset represents a first estimated brain shift, the first estimated brain shift corresponding to a brain shift caused by opening the first burr hole in the cranium;
- f) calculating, by the processor, a first updated brain image dataset from the initial brain image dataset and the first brain shift dataset;
- g) updating, by the processor, the first initial planned trajectory based on the first updated brain image dataset to generate a first updated planned trajectory;
- h) acquiring, at the processor, a second burr hole dataset for a second initial planned trajectory of the plurality of initial planned trajectories, the second burr hole dataset representing a size and a location of a second burr hole in the cranium corresponding to the second initial planned trajectory for a second catheter of the plurality of catheters;
- i) calculating, by the processor, a second brain shift dataset from the first updated brain image dataset, the patient orientation dataset and the second burr hole dataset, wherein the second brain shift dataset at least represents a second estimated brain shift, the second estimated brain shift corresponding to a brain shift caused by opening the second burr hole in the cranium;
- j) updating, by the processor, the first updated brain image dataset based on the second brain shift dataset to generate a second updated brain image dataset; and
- k) updating, by the processor, the second initial planned trajectory based on the second updated brain image dataset to generate a second updated planned trajectory and updating the first updated planned trajectory based on the second updated brain image dataset.

3. The method according to claim 2, wherein the processor is configured to
- select a third initial planned trajectory for a third catheter from among the plurality of initial planned trajectories, the third initial planned trajectory being different from the first and second initial planned trajectories and the third catheter being different than the first catheter and the second catheter;
- perform steps h), i), and j) with respect to the third initial planned trajectory; and
- update the first updated planned trajectory updated in step k), the second updated planned trajectory, and the third initial planned trajectory based on a third updated brain image dataset generated based on a third brain shift dataset.

4. The method according to claim 2, wherein the second brain shift dataset calculated by the processor in step i) also represents a brain shift corresponding to displacement caused by the first catheter.

5. The method according to claim 2, wherein the second brain shift dataset calculated by the processor in step i) also represents a brain shift corresponding to displacement caused by an infusion performed using the first catheter.

6. The method according to claim 2, wherein calculating the second brain shift dataset by the processor in step i) involves considering structural properties of the first catheter.

7. The method according to claim 2, wherein updating the second trajectory by the processor in step k) involves considering structural properties of at least one of the first or second catheter.

8. The method according to claim 2, further comprising amending the second burr hole dataset and repeating steps h) to k) based on the amended second burr hole dataset.

9. The method according to claim 2, further comprising the steps of acquiring, at the processor, a treatment plan and updating, by the processor, the treatment plan based on updated planned trajectories.

10. The method according to claim 2, further comprising the step of checking, by the processor, at least one of the first updated planned trajectory or the second updated planned trajectory for compliance with planning guidelines representing constraints for trajectories.

11. The method according to claim 2, wherein
- if a first set of catheters comprising more than one catheter is planned for insertion through the first burr hole, then updating the first initial planned trajectory by the processor in step g) involves updating, by the processor, initial planned trajectories for all catheters of the first set of catheters; or
- if a second set of catheters comprising more than one catheter is planned for insertion through the second burr hole, then updating the second initial planned trajectory by the processor in step k) involves updating, by the processor, initial planned trajectories for all catheters of the second set of catheters.

12. The method according to claim 11, wherein updating the initial planned trajectories for all catheters of the first set of catheters or the second set of catheters is performed sequentially.

13. A non-transitory, computer-readable storage medium storing instructions for computer program which, when running on a computer, causes the computer to perform a computer implemented medical method for planning trajectories for a plurality of catheters, wherein each planned trajectory runs through a portion of a cranium and a portion of a brain located in the cranium to a respective planned target point in the brain, the instructions causing the computer to perform the following steps:
- a) acquiring, at the processor, an initial brain image dataset, the initial brain image dataset representing a three-dimensional image of at least a part of the brain;
- b) acquiring, at the processor, an initial planning dataset that includes a plurality of initial planned trajectories respectively corresponding to the plurality of catheters;
- c) acquiring, at the processor, a patient orientation dataset that indicates an orientation of the cranium;
- d) acquiring, at the processor, a first burr hole dataset for a first initial planned trajectory of the plurality of initial planned trajectories, the first burr hole dataset representing a size and a location of a first burr hole in the cranium corresponding to the first initial planned trajectory for a first catheter of the plurality of catheters;
e) calculating, by the processor, a first brain shift dataset from the initial brain image dataset, the patient orientation dataset and the first burr hole dataset, wherein the first brain shift dataset at least represents a first estimated brain shift, the first estimated brain shift corresponding to a brain shift caused by opening the first burr hole in the cranium;
f) calculating, by the processor, a first updated brain image dataset from the initial brain image dataset and the first brain shift dataset;
g) updating, by the processor, the first initial planned trajectory based on the first updated brain image dataset to generate a first updated planned trajectory ;
h) acquiring, at the processor, a second burr hole dataset for a second initial planned trajectory of the plurality of initial planned trajectories, the second burr hole dataset representing a size and a location of a second burr hole in the cranium corresponding to the second initial planned trajectory for a second catheter of the plurality of catheters;
i) calculating, by the processor, a second brain shift dataset from the first updated brain image dataset, the patient orientation dataset and the subsequent burr hole dataset, wherein the second brain shift dataset represents a second estimated brain shift, the second estimated brain shift corresponding to a brain shift caused by opening the second burr hole in the cranium;
j) updating, by the processor, the first updated brain image dataset based on the second brain shift dataset to generate a second updated brain image dataset; and
k) updating, by the processor, the first updated planned trajectory and the second initial planned trajectory based on the second updated brain image dataset.

14. A computer comprising the non-transitory computer-readable storage medium according to claim 13.

* * * * *